United States Patent [19]

Slater

[11] 4,201,217
[45] May 6, 1980

[54] NOSTRIL EXPANDER

[76] Inventor: Robert L. Slater, 7102 Grenlock Dr., Sylvania, Ohio 43560

[21] Appl. No.: 923,979

[22] Filed: Jul. 12, 1978

[51] Int. Cl.$^2$ ............................................. A61M 29/00
[52] U.S. Cl. .................................................... 128/342
[58] Field of Search ........... 128/341, 342, 345, 140 N, 128/136

[56]  References Cited
U.S. PATENT DOCUMENTS

| 1,069,459 | 8/1913 | Myles | 128/342 |
| 1,597,331 | 8/1926 | Thurston et al. | 128/342 |

FOREIGN PATENT DOCUMENTS

| 270724 | 2/1914 | Fed. Rep. of Germany | 128/342 |
| 165537 | 3/1920 | United Kingdom | 128/342 |

Primary Examiner—Dalton L. Truluck
Attorney, Agent, or Firm—W. Preston Hickey

[57] ABSTRACT

A nostril enlarging device comprising a generally U-shaped member having a pair of upstanding legs with each leg having a posterior protuberance for locking into the cavity in the lower posterior nostril wall. Each leg also includes an anterior protuberance located upwardly from the posterior protuberance, so that the angle connecting the two is at approximately 45 degrees to the vertical center line of the device.

6 Claims, 3 Drawing Figures

U.S. Patent
May 6, 1980
4,201,217
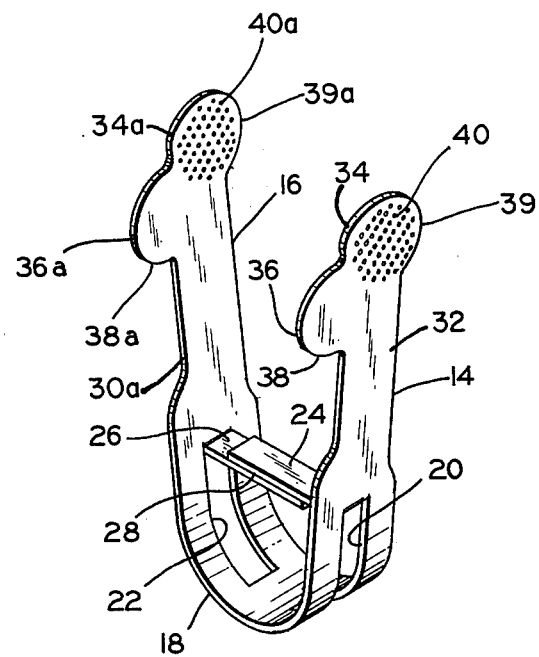
FIG. 1
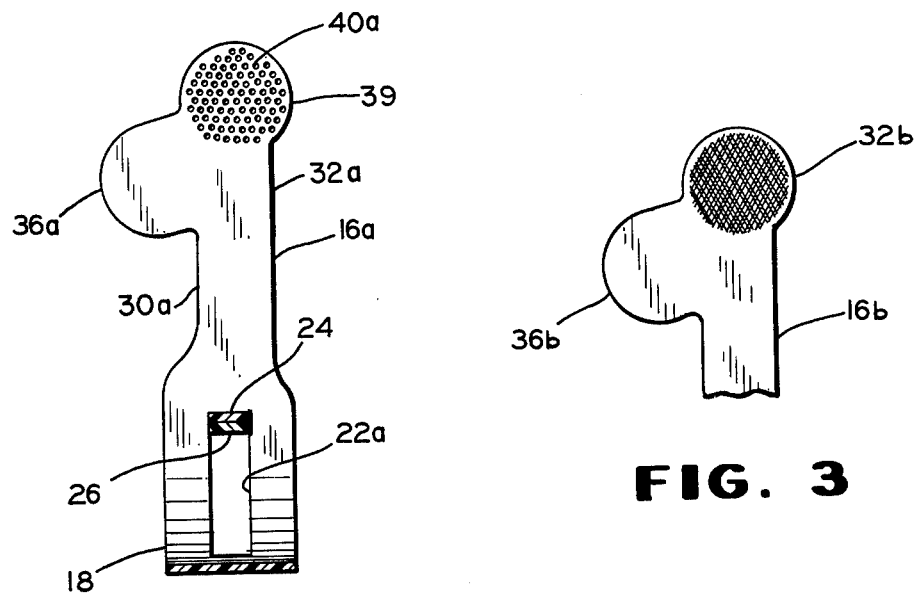
FIG. 2
FIG. 3

NOSTRIL EXPANDER

BACKGROUND OF THE INVENTION

Numerous uses exist for a device which will expand the air passages of the nostrils, particularly adjacent the inlet. One such use I have discovered is the prevention of snoring; another is that of an aid to deep breathing; and still another is that of an aid after surgery for keeping the nostrils open.

I have discovered that snoring is induced by blockage or partial blockage of the inlet to the nasal cavities during sleeping, whereby the system causes air to be taken in through the relaxed passageways of the mouth and throat. In this relaxed condition, these passageways vibrate during the inhalation process to cause snoring. I have further discovered that by holding the entrance to the nostrils open, snoring is prevented.

Accordingly, an object of the present invention is the provision of a new and improved nostril enlarging device that will not fall out of the nasal passages during sleep.

Another object of the present invention is the provision of a device of the above described type, which can be put into the nose and rotated to lock in position.

A further object of the present invention is the provision of a new and improved device of the above described types which is appropriately formed so that it cannot be inadvertently driven too far into the nostrils to hurt the wearer during sleep.

A still further object of the present invention is the provision of a new and improved devide of the above described type which is simple in design, rugged in construction, and inexpensive to manufacture.

Still further objects and advantages of the invention will become apparent to those skilled in the art to which the invention relates from the following description of several preferred embodiments described with reference to the accompanying drawings forming a part of this specification.

BRIEF DESCRIPTION OF THE DRAWINGS

FIG. 1 is an isometric view of one embodiment of the nostril expanding device of the present invention.

FIG. 2 is a sectional view taken on the center line of the device.

FIG. 3 is a fragmentary view showing another embodiment of gripping surface.

DESCRIPTION OF THE PREFERRED EMBODIMENTS

The embodiment of nostril enlarging device shown in the drawings is stamped or otherwise made from a single strip of sheet plastic approximately ⅜ inch wide, 0.010 inch thick, and 4 inches long. The strip of material is bent into a U-shape to provide a pair of upstanding legs 14 and 16, respectively, connected by a rounded base portion 18. In the embodiments shown, the rounded base portion 18 has two rectangular openings 20 and 22 formed therein by slitting material on three sides of the opening to leave the tabs 24 and 26 so made integrally connected at their upper ends with the respective upstanding legs of the device. The tabs 24 and 26 are bent laterally and joined to provide a bridge 28 which perform several functions that will later be described.

As best seen in FIG. 1, the upstanding legs 14 and 16 are mirror images of each other, and each has a posterior side edge 30, an anterior side edge 32, and an upper end edge 34. The surfaces of the leg 16 carry the same designation as to do the surfaces of the leg 14, excepting that a subscript "a" is affixed thereto.

It is intended that the legs of the device so far described be pressed toward each other and slipped into the nostrils of a human. When released, the legs bias the opposing side surfaces of the nostrils apart to enlarge the nostril openings. Accordingly, the bridge 28 is sized to hold the opposing side edges apart by the proper distance when the bridge is adjacent the bottom of the nose. The legs 14 and 16 are sufficiently flexible that they bend to conform to the tapered opposing side surfaces of the nostril and yieldingly supply a sufficient pressure thereto to hold the opposing sides of the nose apart. To this end, the legs 14 and 16 are necked down in the region upwardly of the bridge to provide increased flexibility in the region which abuts the thin walled portions of the nostrils that are located just upwardly of the thickened entrance portion of the nose.

According to further principles of the present invention, the device is prevented from springing out of the nostrils by protuberances 36 and 36a on the posterior edges of the legs which are located to conform to the lower posterior nostril cavities. The posterior protuberances have a rounded lower surface 38 which conforms to the lower walls of the stated nasal cavities to prevent the device from moving directly downwardly out of the nostril. In order to prevent the posterior protuberances 36 and 36a from working forwardly out of the stated cavities; each leg is also provided with an anterior protuberance 39 on the anterior side edge of the leg for abutting the anterior wall of the nostril when the posterior protuberance is positioned in the stated cavity. In order to aid the insertion and removal of the device, the anterior protuberances 38a and 39 and 39a, are located upwardly of the posterior protuberances so that the 45 degree line connecting the center of the anterior and posterior protuberances lies at approximately 45 degrees to the vertical center line of the device. This allows the device to be inserted into the nostrils when the device is positioned at approximately a 30 degree angle to the vertical and to be locked into position by rotating the device thereafter past the vertical position with the bridge adjacent the bottom of the nose. It will be seen that the distance between the opposite edges of the anterior and posterior protuberances on the 45 degree line is greater than the distance between the edge of the posterior protuberance 36 and the anterior edge of the leg 14 taken normal to the vertical axis of the device. This gives a type of locking action when the bottom of the device is rotated posteriorly to bring the bottom of this device adjacent the lip of the wearer. It will be seen that during sleep, the forces against the face of the wearer will normally push the bottom of the device against the lip so that the device normally stays in the locked position.

To further aid in the locking action, the upper end portions of the legs 14 and 16 may have a plurality of closely spaced openings 40 therethrough to provide a gripping surface with the outer walls of the nostrils. Inasmuch as these surfaces of the legs are biased outwardly against the membranes of the nostril, the membranes will gradually sink into the openings 40 to provide a further gripping action. In addition to this gripping action, the plurality of openings 40 will permit air to pass through the legs to the membranes, so that the membranes can "breathe" and so that evaporation of moisture from the walls can take place. In some instances, the openings 40 may be replaced by a pattern of suitably shaped dimples, as for example, diamond shaped, round, etc., which will embed slightly into the membranes to provide the gripping action.

FIG. 3 is a fragmentary view of another embodiment having a criss crossing pattern of diamond shaped projections as a gripping surface. The diamonds project above the surrounding surfaces.

It will be apparent that the device above described can be molded as well as stamped, and that numerous modifications in design can be made without departing from the spirit or scope of the invention. One such embodiment, of course, would be to make the device from appropriately bent metal or plastic wire. The device can also be made from suitably coated metal. The openings 20 and 22 need not be provided in all instances, and the precise contours need not be strictly adhered to. The bridge 28 need not be rigid or used in all instances, but the combination of the bridge and the openings 20 and 22 causes a hinging action whereby the legs 14 and 16 rotate slightly opposite the bridge as the upper ends of the legs are pushed together.

While it is not to be preferred, the posterior and anterior protuberances can be formed from a properly shaped wire, the center portion of which is U-shaped to provide legs 14 and 16. The center section of the wire may be flattened to simulate the bridge 28. Such a wire will conform generally in outline with that of the solid device previously described. Also, while it is not to be preferred, the outward biasing of the legs 14 and 16 may be produced by a small lead screw extending between the legs, rather than by the spring action of the legs that has been previously described.

While the invention has been described in considerable detail, I do not wish to be limited to the particular embodiments shown and described, and it is my intention to cover hereby all novel adaptations, modifications, and arrangements thereof which come within the practice of those skilled in the art to which the invention relates, and which fall within the purview of the following claims.

I claim:

1. A nostril enlarging device comprising: a U-shaped member of sheet material with flexible upstanding legs having anterior, posterior, and upper end side edges; said posterior side edge of each leg having a rounded protuberance for locking into the lower posterior nostril cavity; said anterior edge of each leg being provided with a rounded protuberance having a lower concave surface for engaging the anterior nostril wall; said anterior protuberances being spaced upwardly from said posterior protuberances so that the angular distance between the edges of the anterior and posterior protuberances is greater than the distance between the edged of the posterior protuberance and the directly opposite anterior edge of the leg; and said legs being constructed and arranged for resilient spreading action.

2. The device of claim 1 having a bridge between said legs spaced from the leg connecting portion of the U-shaped spring member.

3. The device of claim 2 wherein the spacing between said bridge and said posterior protuberances is such that the bridge abuts the bottom of a nose when said posterior protuberances are located in the lower posterior nostril cavities.

4. The device of claim 2 wherein material is removed from the leg connecting portion below said bridge to make the leg connecting portion less rigid.

5. A nostril enlarging device comprising: a generally U-shaped spring member having upstanding legs with posterior and anterior side edges and a connecting base; said posterior and anterior side edges having rounded protuberances with the anterior protuberance being positioned upwardly of the posterior protuberance so that the angular distance between the edges of the protuberances is greater than the width of the leg at the posterior protuberance.

6. The device of claim 5 including a stop spaced beneath said posterior protuberance to be adjacent the bottom of the nose when said posterior protuberance is in the lower posterior nostril cavity.

* * * * *